(12) United States Patent
Jing et al.

(10) Patent No.: US 10,898,613 B2
(45) Date of Patent: Jan. 26, 2021

(54) HYALURONIC ACID GEL WITH A DIVALENT ZINC CATION

(71) Applicant: Nestlé Skin Health SA, Lausanne (CH)

(72) Inventors: Laura Jing Jing, Antibes (FR); Craig Steven Harris, Biot (FR); Anders Karlsson, Storvreta (SE); Elin Säwén, Sollentuna (SE)

(73) Assignee: NESTLÉ SKIN HEALTH SA, Lausanne (CH)

( * ) Notice: Subject to any disclaimer, the term of this patent is extended or adjusted under 35 U.S.C. 154(b) by 0 days.

(21) Appl. No.: 16/335,093

(22) PCT Filed: Sep. 20, 2017

(86) PCT No.: PCT/EP2017/073823
§ 371 (c)(1),
(2) Date: Mar. 20, 2019

(87) PCT Pub. No.: WO2018/055002
PCT Pub. Date: Mar. 29, 2018

(65) Prior Publication Data
US 2019/0351105 A1    Nov. 21, 2019

(30) Foreign Application Priority Data
Sep. 21, 2016 (EP) .................... 16189972

(51) Int. Cl.
| | | |
|---|---|---|
| A61L 27/52 | (2006.01) | |
| A61L 27/20 | (2006.01) | |
| C08B 37/00 | (2006.01) | |
| C08L 5/08 | (2006.01) | |
| A61P 43/00 | (2006.01) | |

(Continued)

(52) U.S. Cl.
CPC ............. *A61L 27/52* (2013.01); *A61L 27/025* (2013.01); *A61L 27/20* (2013.01); *A61L 27/54* (2013.01);
(Continued)

(58) Field of Classification Search
None
See application file for complete search history.

(56) References Cited

U.S. PATENT DOCUMENTS

| | | |
|---|---|---|
| 2012/0108537 A1 | 5/2012 | Bourdon |
| 2014/0088037 A1 | 3/2014 | Bon Betemps et al. |
| 2016/0303024 A1 | 10/2016 | Bon Betemps et al. |

FOREIGN PATENT DOCUMENTS

| | | |
|---|---|---|
| FR | 2945293 A1 | 11/2010 |
| FR | 2979539 A1 | 3/2013 |

(Continued)

OTHER PUBLICATIONS

JP3779200B2 Google English translation ([retrieved from on-line website: https://patents.google.com/patent/JP3779200B2/en]). (Year: 2006).*

(Continued)

*Primary Examiner* — Kyung S Chang
(74) *Attorney, Agent, or Firm* — Foley & Lardner LLP; Sunit Talapatra (57) ABSTRACT

A method of preparing a sterilized injectable hydrogel composition, including the steps: a) covalently crosslinking a glycosaminoglycan using a bi- or polyfunctional crosslinking agent to form a covalently crosslinked glycosaminoglycan, b) swelling the covalently crosslinked glycosaminoglycan in a solution including a divalent cation to form a hydrogel composition, and c) sterilizing the hydrogel composition by autoclaving to form a sterilized injectable hydrogel composition, and to sterilized injectable hydrogel compositions obtainable by such method.

16 Claims, 6 Drawing Sheets

(51) Int. Cl.
  *A61P 17/00* (2006.01)
  *A61P 23/02* (2006.01)
  *A61L 2/00* (2006.01)
  *A61L 27/02* (2006.01)
  *A61L 27/54* (2006.01)
  *A61L 27/58* (2006.01)

(52) U.S. Cl.
  CPC ......... *A61L 27/58* (2013.01); *A61L 2300/102* (2013.01); *A61L 2400/06* (2013.01)

(56) References Cited

FOREIGN PATENT DOCUMENTS

| FR | 2979539 | A1 | 3/2013 |
| FR | 3032617 | A1 | 8/2016 |
| FR | 3032617 | A1 | 8/2016 |
| JP | 2003160464 | A | 6/2003 |
| JP | 3779200 | B2 * | 5/2006 |
| WO | 9010020 | A1 | 9/1990 |
| WO | WO-90/10020 | A1 | 9/1990 |
| WO | 9704012 | A1 | 2/1997 |
| WO | 0027887 | A2 | 5/2000 |
| WO | 2014032804 | A1 | 3/2014 |

OTHER PUBLICATIONS

International Search Report and Written Opinion issued in corresponding International Patent Application No. PCT/EP2017/073823, 15 pages. (Dec. 11, 2017).

Database WPI / Thompson Scientific, London, Great Britain, AN JP2003-818778A (Denki Kagaku Kogyo KK), Week 200377.

* cited by examiner

HYALURONIC ACID GEL WITH A DIVALENT ZINC CATION

FIELD OF THE INVENTION

The present invention relates to the field of injectable hydrogel compositions and the use of such compositions in medical and/or cosmetic applications.

BACKGROUND

One of the most widely used biocompatible polymers for medical use is hyaluronic acid (HA). It is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical crosslinking of polymers to infinite networks. While native hyaluronic acid and certain crosslinked hyaluronic acid products absorb water until they are completely dissolved, crosslinked hyaluronic acid gels typically absorb a certain amount of water until they are saturated, i.e. they have a finite liquid retention capacity, or swelling degree.

Since hyaluronic acid is present with identical chemical structure except for its molecular mass in most living organisms, it gives a minimum of reactions and allows for advanced medical uses. Crosslinking and/or other modifications of the hyaluronic acid molecule is necessary to improve its duration in vivo. Furthermore, such modifications affect the liquid retention capacity of the hyaluronic acid molecule. As a consequence thereof, hyaluronic acid has been the subject of many modification attempts.

Hyaluronic salts with divalent cations, e.g. zink hyaluronate and calcium hyaluronate are known in the field, e.g. through the patent family WO9010020A1, and zinc hyaluronan is sold under the name Curiosin® for promoting physiological wound healing and preventing wound infection.

FR 2 979 539 A1 discloses compositions comprising hyaluronic acid, an anesthetic, an α-lipoic acid and a cupper salt. One possible composition is comprising a cross-linked hyaluronic acid and further 0.006 mg/mL (0.027 mM) zinc acetate dihydrate. The composition is sterilized by autoclaving.

FR 3 032 617 A1 discloses a process for preparing a cross-linked hyaluronic acid or a salt thereof using the cross-linking agent 1,4-butanediol diglycidyl ether (BDDE). The salt may be a sodium, calcium, zinc or potassium salt. The process is involving a step of reacting residual BDDE with nucleophiles after the cross-linking step, followed by a washing step. The process may involve sterilization by autoclaving in an unspecified aqueous environment.

DESCRIPTION OF THE INVENTION

An object of the present invention is to provide improved injectable hydrogel compositions, preferably hyaluronic acid based hydrogel compositions comprising divalent cations, preferably $Zn^{2+}$, for use as dermal fillers and/or for slow release of the divalent cations in a subject.

An object of the present invention is to provide improved injectable hydrogel compositions, preferably hyaluronic acid based hydrogel compositions comprising divalent cations, preferably $Zn^{2+}$, which exhibit decreased degradation of the composition during autoclaving.

An object of the present invention is to provide improved injectable hydrogel compositions, preferably hyaluronic acid based hydrogel compositions comprising divalent cations, preferably $Zn^{2+}$, which exhibit increased stability after autoclaving.

An object of the present invention is to provide improved injectable hydrogel compositions, preferably hyaluronic acid based hydrogel compositions comprising divalent cations, preferably $Zn^{2+}$, which upon injection of the composition in a subject provide a slow and safe release of the divalent cations to the subject.

Hydrogel compositions, such as hyaluronic acid based hydrogel compositions, for use in injection need to be sterilized before use. Sterilization is generally performed by heat treatment, such as autoclaving. The heat treatment generally leads to a reduction of the rigidity or viscosity of the composition.

One problem which has been observed with prior art hyaluronic acid compositions comprising zink, is that the compositions exhibit increased degradation of the hyaluronic acid during autoclaving and decreased stability of the composition after autoclaving as compared to identical compositions with sodium as the counterion. Thus, although an initial stabilization (i.e. increased viscosity or G') of the composition is achieved due to electrostatic interaction between the positively charged $Zn^{2+}$ and negatively charged hyaluronate, this stabilizing is decreased or eliminated due to degradation of the hyaluronate during autoclaving. This in turn decreases the longevity of the compositions in vivo.

According to aspects illustrated herein, there is provided a method of preparing a sterilized injectable hydrogel composition, comprising the steps:
 a) covalently crosslinking a glycosaminoglycan using a bi- or polyfunctional crosslinking agent to form a covalently crosslinked glycosaminoglycan, and
 b) swelling the covalently crosslinked glycosaminoglycan in a solution comprising a divalent cation to form a hydrogel composition, and
 c) sterilizing the hydrogel composition by autoclaving to form a sterilized injectable hydrogel composition.

The term "injectable" means that the composition is provided in a form which is suitable for parenteral injection, e.g. into soft tissue, such as skin, of a subject or patient. An injectable composition should be sterile and free from components that may cause adverse reactions when introduced into soft tissue, such as the skin, of a subject or patient. This implies that no, or only very mild, immune response occurs in the treated individual. That is, no or only very mild undesirable local or systemic effects occur in the treated individual.

According to some embodiments, the glycosaminoglycan is selected from the group consisting of hyaluronic acid, chondroitin and chondroitin sulfate, and mixtures thereof. In a preferred embodiment, the glycosaminoglycan is hyaluronic acid.

The divalent cation is preferably selected from the group consisting of $Ca^{2+}$, $Cu^{2+}$, $Mg^{2+}$ and $Zn^{2+}$. In a preferred embodiment, the divalent cation is $Zn^{2+}$.

In some embodiments, the $Zn^{2+}$ in the solution is provided by a Zn-salt selected from the group consisting of $ZnCl_2$, Zn-gluconate and Zn-citrate.

The present inventors have identified that in a hyaluronic acid gel composition, $Zn^{2+}$ in a concentration in the range of 0.05 to 4 mM, and preferably in the range of 0.05 to 2 mM acts to stabilize the composition, whereas higher concentrations of $Zn^{2+}$ instead cause degradation of the composition. Thus, in some embodiments, the concentration of the divalent cation in the solution is in the range of 0.05 to 4 mM, preferably in the range of 0.05 to 2 mM. In further preferred embodiments, the concentration of $Zn^{2+}$ is in the range of 0.5 to 4 mM, preferably in the range of 0.5 to 2 mM, more preferably in the range of 0.8 to 4 mM, such as 0.8 to 2 mM. In alternative preferred embodiments, the concentration of $Zn^{2+}$ is in the range of 0.8 to 1.5 mM, and preferably in the range of 0.8 to 1.2 mM, more preferably about 1.0 mM.

The viscosity and/or elastic modulus G' of the composition hydrogel composition may be measured according to various methods, well known to the person skilled in the art. Viscosity may for example be measured as the "Zero shear viscosity, $\eta_0$" by rotational viscometry using a Bohlin VOR rheometer (Measuring system C14 or PP 30, Gap 1.00 mm). Other methods of measuring viscosity may also be applicable. The elastic modulus G' may for example be measured using a Bohlin VOR Reometer (Measure system PP 30, Gap 1.00 mm) by performing a strain sweep to find the linear viscoelastic region (LVR) and then measuring the viscoelastic properties within the LVR. Other methods of measuring elastic modulus G' may also be applicable.

The composition may be present in an aqueous form, but it may also be present in dried or precipitated form, e.g. in ethanol.

The glycosaminoglycan of the composition is preferably a hyaluronic acid. Unless otherwise provided, the term "hyaluronic acid" encompasses all variants and combinations of variants of hyaluronic acid, hyaluronate or hyaluronan, of various chain lengths and charge states, as well as with various chemical modifications, including crosslinking. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —$CH_2OH$ groups to —CHO and/or —COOH; periodate oxidation of vicinal hydroxyl groups, optionally followed by reduction, e.g. reduction of —CHO to —$CH_2OH$ or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings.

In some embodiments, the glycosaminoglycan in step a) of the method is provided in the form of a salt with a monovalent cation, e.g. $Na^+$.

The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

In certain embodiments the concentration of the glycosaminoglycan is in the range of 1 to 100 mg/ml. In some embodiments the concentration of the glycosaminoglycan is in the range of 2 to 50 mg/ml. In specific embodiments the concentration of the glycosaminoglycan is in the range of 5 to 30 mg/ml or in the range of 10 to 30 mg/ml.

The glycosaminoglycan is covalently crosslinked. Crosslinking of the glycosaminoglycan may be achieved by modification with a crosslinking agent. The crosslinking agent may for example selected from the group consisting of divinyl sulfone, multiepoxides and diepoxides. According to embodiments the crosslinking agent is selected from the group consisting of 1,4-butanediol diglycidyl ether (BDDE), 1,2-ethanediol diglycidyl ether (EDDE) and diepoxyoctane. According to a preferred embodiment, the crosslinking agent is 1,4-butanediol diglycidyl ether (BDDE).

The sterilized injectable composition formed using the inventive method is a hydrogel. That is, it can be regarded as a water-insoluble, but substantially dilute crosslinked system of glycosaminoglycan molecules when subjected to a liquid, typically an aqueous liquid.

The sterilized injectable hydrogel composition contains mostly liquid by weight and can e.g. contain 90-99.9% water, but it behaves like a solid due to a three-dimensional crosslinked hyaluronic acid network within the liquid. Due to its significant liquid content, the gel is structurally flexible and similar to natural tissue, which makes it very useful as a scaffold in tissue engineering and for tissue augmentation.

The hydrogel composition is preferably biocompatible. This implies that no, or only very mild, immune response occurs in the treated individual. That is, no or only very mild undesirable local or systemic effects occur in the treated individual.

As mentioned, crosslinking of a glycosaminoglycan such as hyaluronic acid, to form the crosslinked glycosaminoglycan, may for example be achieved by modification with a crosslinking agent, for example BDDE (1,4-butandiol diglycidylether). The glycosaminoglycan concentration and the extent of crosslinking affects the mechanical properties, e.g. the elastic modulus G', and stability properties of the hydrogel. Crosslinked glycosaminoglycan gels are often characterized in terms of "degree of modification".

The degree of modification of hyaluronic acid gels generally range between 0.1 and 15 mole %.

In some embodiments the hyaluronic acid gel has a degree of modification of 12 mole % or less, such as 12 mole % or less, such as 10 mole % or less, for example in the range of 0.1 to 12 mole %, such as in the range of 0.2 to 10 mole %, such as in the range of 0.3 to 8 mole %.

In some embodiments, the hyaluronic acid gel has a degree of modification of 2 mole % or less, such as 1.5 mole % or less, such as 1.25 mole % or less, for example in the range of 0.1 to 2 mole %, such as in the range of 0.2 to 1.5 mole %, such as in the range of 0.3 to 1.25 mole %.

The degree of modification (mole %) describes the amount of crosslinking agent(s) that is bound to glycosaminoglycan, i.e. molar amount of bound crosslinking agent(s) relative to the total molar amount of repeating glycosaminoglycan disaccharide units. The degree of modification reflects to what degree the glycosaminoglycan has been chemically modified by the crosslinking agent. Reaction conditions for crosslinking and suitable analytical techniques for determining the degree of modification are all well known to the person skilled in the art, who easily can adjust these and other relevant factors and thereby provide suitable conditions to obtain a degree of modification in the range of 0.1-15% and verify the resulting product characteristics with respect to the degree of modification. A BDDE (1,4-butandiol diglycidylether) crosslinked hyaluronic acid gel may for example be prepared according to the method described in Examples 1 and 2 of published international patent application WO 9704012.

In a preferred embodiment the crosslinked glycosaminoglycan of the composition is present in the form of a crosslinked hyaluronic acid crosslinked by a crosslinking agent, wherein the concentration of said hyaluronic acid is in the range of 2 to 50 mg/ml and the degree of modification with said crosslinking agent is in the range of 0.1 to 2 mole %.

In some embodiments, the solution further comprises a buffering compound. The purpose of the buffering compound is to maintain the pH of the composition at a suitable value, typically in the range of 5 to 8, preferably in the range of 6 to 7.5. Thus, the pH value of the solution is in the range of 5 to 8, preferably in the range of 6 to 7.5.

The injectable hydrogel composition may further comprise a therapeutically relevant concentration of a local anesthetic. A local anesthetic is a drug that causes reversible local anesthesia and a loss of nociception. When it is used on specific nerve pathways (nerve block), effects such as analgesia (loss of pain sensation) and paralysis (loss of muscle power) can be achieved. The local anesthetic may be added to the composition to reduce pain or discomfort experienced by the patient due to the injection procedure.

According to certain embodiments the local anesthetic is selected from the group consisting of amide and ester type local anesthetics, for example bupivacaine, butanilicaine, carticaine, cinchocaine (dibucaine), clibucaine, ethyl para-piperidinoacetylaminobenzoate, etidocaine, lignocaine (lidocaine), mepivacaine, oxethazaine, prilocaine, ropivacaine, tolycaine, trimecaine, vadocaine, articaine, levobupivacaine, amylocaine, cocaine, propanocaine, clormecaine, cyclomethycaine, proxymetacaine, amethocaine (tetracaine), benzocaine, butacaine, butoxycaine, butyl am inobenzoate, chloroprocaine, dimethocaine (larocaine), oxybuprocaine, piperocaine, parethoxycaine, procaine (novocaine), propoxycaine, tricaine or a combination thereof. According to some embodiments the local anesthetic is selected from the group consisting of lidocaine and ropivacaine, or a combination thereof.

According to specific embodiments the local anesthetic is lidocaine. Lidocaine is a well-known substance, which has been used extensively as a local anesthetic in injectable formulations, such as hyaluronic acid compositions. The concentration of the amide or ester local anesthetic may be selected by the skilled person within the therapeutically relevant concentration ranges of each specific local anesthetic or a combination thereof.

In some embodiments the concentration of said local anesthetic is in the range of 0.1 to 30 mg/ml. In certain embodiments the concentration of said local anesthetic is in the range of 0.5 to 10 mg/ml.

When lidocaine is used as the local anesthetic, the lidocaine may preferably be present in a concentration in the range of 1 to 5 mg/ml, more preferably in the range of 2 to 4 mg/ml, such as in a concentration of about 3 mg/ml.

When ropivacaine is used as the local anesthetic, the ropivacaine may preferably be present in a concentration in the range of 0.1 to 3 mg/ml, more preferably in the range of 0.5 to 2 mg/ml, such as in a concentration of about 1 mg/ml.

The method described herein involves sterilization of the composition by autoclaving, i.e sterilization using saturated steam. The autoclaving may be performed at an $F_0$-value>4. The autoclaving may preferably be performed at an $F_0$-value in the range of 10 to 50. The $F_0$ value of a saturated steam sterilisation process is the lethality expressed in terms of the equivalent time in minutes at a temperature of 121° C. delivered by the process to the product in its final container with reference to microorganisms posessing a Z-value of 10.

In a preferred embodiment, the glycosaminoglycan is hyaluronic acid at a concentration in the range of 2-50 mg/ml, the divalent cation is $Zn^{2+}$ at a concentration in the range of 0.05 to 4 mM, preferably in the range of 0.05 to 2 mM, and sterilization is performed by autoclaving at an $F_0$-value>4.

Experimental data provided by the inventors show that the sterilized injectable hydrogel compositions formed according to the inventive method exhibit increased stability compared to identical compositions without the divalent cation.

The term stability, as used herein, is used to denote the ability of the sterilized injectable hydrogel composition to resist degradation during storage and handling prior to use. It is known that the addition of constituents to a glycosaminoglycan, such as hyaluronic acid or hyaluronic acid gel, may affect the stability of said glycosaminoglycan. Stability of a hydrogel composition comprising a glycosaminoglycan can be determined by a range of different methods. Methods for determining stability include, but are not limited to, assessing homogeneity, color, clarity, pH, gel content and rheological properties of the composition. Stability of a hydrogel composition comprising a glycosaminoglycan is often determined by observing or measuring one or more of said parameters over time. Stability may for example be determined by measuring the viscosity and/or elastic modulus G' of the composition over time. Viscosity may for example be measured as the "Zero shear viscosity, $\eta_0$" by rotational viscometry using a Bohlin VOR rheometer (Measuring system C14 or PP 30, Gap 1.00 mm). Other methods of measuring viscosity may also be applicable. The elastic modulus G' may for example be measured using a Bohlin VOR Reometer (Measure system PP 30, Gap 1.00 mm) by performing a strain sweep to find the linear viscoelastic region (LVR) and then measuring the viscoelastic properties within the LVR. Other methods of measuring elastic modulus G' may also be applicable.

According to aspects illustrated herein, there is provided a sterilized injectable hydrogel composition obtainable by the method described above.

According to aspects illustrated herein, there is provided a sterilized injectable hydrogel composition comprising
  i) a covalently crosslinked glycosaminoglycan, and
  ii) a divalent cation.

In some embodiments, the glycosaminoglycan is selected from the group consisting of hyaluronic acid, chondroitin and chondroitin sulfate, and mixtures thereof. In a preferred embodiment, the glycosaminoglycan is a hyaluronic acid.

The crosslinking agent may be selected from the group consisting of divinyl sulfone, multiepoxides and diepoxides. In some embodiments, the crosslinking agent is selected from the group consisting of 1,4-butanediol diglycidyl ether (BDDE), 1,2-ethanediol diglycidyl ether (EDDE) and diepoxyoctane. In a preferred embodiment, the crosslinking agent is 1,4-butanediol diglycidyl ether (BDDE).

In some embodiments, the covalently crosslinked glycosaminoglycan has a degree of modification of 2 mole % or less, such as 1.5 mole % or less, such as 1.25 mole % or less.

In some embodiments, the covalently crosslinked glycosaminoglycan has a degree of modification in the range of 0.1 to 2 mole %, such as in the range of 0.2 to 1.5 mole %, such as in the range of 0.3 to 1.25 mole %.

In some embodiments, the concentration of the glycosaminoglycan in the composition is in the range of 1 to 100 mg/ml.

In some embodiments, the concentration of the glycosaminoglycan in the composition is in the range of 2 to 50 mg/ml.

In some embodiments, the concentration of the glycosaminoglycan in the composition is in the range of 10 to 30 mg/ml.

In some embodiments, the divalent cation is selected from the group consisting of $Ca^{2+}$, $Cu^{2+}$, $Mg^{2+}$ and $Zn^{2+}$. In a preferred embodiment, the divalent cation is $Zn^{2+}$.

The concentration of the divalent cation in the composition is preferably in the range of 0.05 to 4 mM, more preferably in the range of 0.05 to 2 mM.

The concentration of the divalent cation zinc in the composition is preferably in the range of 0.05 to 4 mM, more preferably in the range of 0.05 to 2 mM. In further preferred embodiments, the concentration of $Zn^{2+}$ is in the range of 0.5 to 4 mM, preferably in the range of 0.5 to 2 mM, more preferably in the range of 0.8 to 4 mM, such as 0.8 to 2 mM. In alternative preferred embodiments, the concentration of $Zn^{2+}$ is in the range of 0.8 to 1.5 mM, and preferably in the range of 0.8 to 1.2 mM, more preferably about 1.0 mM. The present inventors have identified that in a hyaluronic acid gel composition, $Zn^{2+}$ in a concentration in these ranges acts to stabilize the composition, whereas higher concentrations of $Zn^{2+}$ instead cause degradation of the composition.

In some embodiments, the composition further comprises a buffering compound. The purpose of the buffering compound is to maintain the pH of the composition at a suitable value, typically in the range of 5 to 8, preferably in the range of 6 to 7.5. Thus, the pH value of the solution is in the range of 5 to 8, preferably in the range of 6 to 7.5.

In some embodiments, the composition further comprises a therapeutically relevant concentration of a local anesthetic.

The local anesthetic is preferably selected from the group consisting of lidocaine and ropivacaine.

The compositions described herein have preferably been subjected to sterilization by autoclaving, i.e sterilization using saturated steam. The autoclaving, may be performed at an $F_0$-value>4. The $F_0$ value of a saturated steam sterilisation process is the lethality expressed in terms of the equivalent time in minutes at a temperature of 121° C. delivered by the process to the product in its final container with reference to microorganisms posessing a Z-value of 10.

The inventive composition preferably exhibits increased stability compared to an identical composition without the divalent cation.

The components, features, effects and advantages of the composition may be further defined as described above with reference to the method of preparing the sterilized injectable hydrogel composition.

The sterilized injectable hydrogel compositions according to the invention may be provided in the form of a pre-filled syringe, i.e. a syringe that is pre-filled with the injectable hydrogel composition and autoclaved.

The sterilized injectable hydrogel compositions as described herein may advantageously be used for the transport or administration and slow or controlled release of various parmaceutical or cosmetic substances.

The sterilized injectable hydrogel compositions described herein may be employed in medical as well as non-medical, e.g. purely cosmetic, procedures by injection of the composition into soft tissues of a patient or subject. The compositions have been found useful in, e.g., soft tissue augmentation, for example filling of wrinkles, by hyaluronic acid gel injection. The compositions have also been found useful in a cosmetic treatment, referred to herein as skin revitalization, whereby small quantities of the hyaluronic acid composition are injected into the dermis at a number of injection sites distributed over an area of the skin to be treated, resulting in improved skin tone and skin elasticity. Skin revitalization is a simple procedure and health risks associated with the procedure are very low.

The composition is useful, for example in the treatment of various dermatological conditions. Particularly, there is provided an injectable hyaluronic acid composition as described above for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteototic eczema. In other words, there is provided an injectable hyaluronic acid composition as described above for use in the manufacture of a medicament for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteototic eczema.

According to other aspects illustrated herein, there is provided the use of an injectable hyaluronic acid composition as described above for cosmetic, non-medical, treatment of a subject by injection of the composition into the skin of the subject. A purpose of the cosmetic, non-medical, treatment may be for improving the appearance of the skin, preventing and/or treating hair loss, filling wrinkles or contouring the face or body of a subject. The cosmetic, nonmedical, use does not involve treatment of any form of disease or medical condition. Examples of improving the appearance of the skin include, but are not limited to, treatment of sun-damaged or aged skin, skin revitalization, skin whitening and treatment of hyper pigmentation disorders such as senile freckles, melasma and ephelides.

According to aspects illustrated herein, there is provided the sterilized injectable hydrogel composition as described herein for use as a medicament.

According to aspects illustrated herein, there is provided the sterilized injectable hydrogel composition as described herein for use in the treatment of a condition susceptible to treatment with the divalent cation.

In some embodiments, the sterilized injectable hydrogel composition is injected into the skin of a subject. The composition preferably provides a slow release of the divalent cation in the skin of the subject upon injection. The release of the divaalent cation in the skin of the subject should be well below the toxic dose of the divalent cation. As an example, for a composition with $Zn^{2+}$ the release in the skin of the subject upon injection is preferably below 0.1 mmol/day.

According to aspects illustrated herein, there is provided the manufacture of a medicament for treatment of a condition susceptible to treatment with the divalent cation.

According to aspects illustrated herein, there is provided a method of treating a patient suffering from a condition susceptible to treatment with a divalent cation by administering to the patient a therapeutically effective amount of the sterilized injectable hydrogel composition according as described herein.

According to aspects illustrated herein, there is provided a method of cosmetically treating skin, which comprises administering to the skin a sterilized injectable hydrogel composition as described herein.

The inventive methods and compositions are described herein particularly with reference to a preferred embodiment, wherein the glycosaminoglycan is hyaluronic acid and the divalent cation is $Zn^{2+}$. However, the invention is not restricted to this particular embodiment. Other glycosaminoglycans and other divalent cations are also contemplated within the scope of the present.

The person skilled in the art realizes that the present invention by no means is limited to the preferred embodiments described herein. On the contrary, many modifications and variations are possible within the scope of the appended claims. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

Itemized Listing of Embodiments

The following is a non-limiting and itemized listing of embodiments of the present disclosure, presented for the purpose of describing various features and combinations provided by the invention in certain of its aspects.

1. A method of preparing a sterilized injectable hydrogel composition, comprising the steps:
   a) covalently crosslinking a glycosaminoglycan using a bi- or polyfunctional crosslinking agent to form a covalently crosslinked glycosaminoglycan, and
   b) swelling the covalently crosslinked glycosaminoglycan in a solution comprising a divalent cation to form a hydrogel composition, and
   c) sterilizing the hydrogel composition by autoclaving to form a sterilized injectable hydrogel composition.
2. The method according to item 1, wherein the glycosaminoglycan is selected from the group consisting of hyaluronic acid, chondroitin and chondroitin sulfate, and mixtures thereof.
3. The method according to item 2, wherein the glycosaminoglycan is a hyaluronic acid.
4. The method according to any one of the preceding items, wherein the glycosaminoglycan in step a) is provided in the form of a salt with a monovalent cation, e.g. $Na^+$.
5. The method according to any one of the preceding items, wherein the crosslinking agent is selected from the group consisting of divinyl sulfone, multiepoxides and diepoxides.
6. The method according to item 5, wherein the crosslinking agent is selected from the group consisting of 1,4-butanediol diglycidyl ether (BDDE), 1,2-ethanediol diglycidyl ether (EDDE) and diepoxyoctane.
7. The method according to item 6, wherein the crosslinking agent is 1,4-butanediol diglycidyl ether (BDDE).
8. The method according to any one of the preceding items, wherein the covalently crosslinked glycosaminoglycan has a degree of modification of 2 mole % or less, such as 1.5 mole % or less, such as 1.25 mole % or less.
9. The method according to any one of the preceding items, wherein the covalently crosslinked glycosaminoglycan has a degree of modification in the range of 0.1 to 2 mole %, such as in the range of 0.2 to 1.5 mole %, such as in the range of 0.3 to 1.25 mole %.
10. The method according to any one of the preceding items, wherein the concentration of said glycosaminoglycan is in the range of 1 to 100 mg/ml, such as in the range of 2 to 50 mg/ml, such as in the range of 10 to 30 mg/ml.
11. The method according to any one of the preceding items, wherein the divalent cation is selected from the group consisting of $Ca^{2+}$, $Cu^{2+}$, $Mg^{2+}$ and $Zn^{2+}$.
12. The method according to any one of the preceding items, wherein the divalent cation is $Zn^{2+}$.
13. The method according to item 12, wherein the $Zn^{2+}$ in the solution is provided by a Zn-salt selected from the group consisting of $ZnCl_2$, Zn-gluconate and Zn-citrate.
14. The method according to any one of the preceding items, wherein the concentration of the divalent cation in the solution is in the range of 0.05 to 4 mM, preferably in the range of 0.05 to 2 mM.
15. The method according to any one of the preceding items, wherein the divalent cation is $Zn^{2+}$; and wherein the concentration of $Zn^{2+}$ in the solution is in the range of 0.5 to 4 mM, preferably in the range of 0.5 to 2 mM, more preferably in the range of 0.8 to 4 mM, such as 0.8 to 2 mM.
16. The method according to item 15, wherein the concentration of $Zn^{2+}$ in the solution is in the range of 0.8 to 1.5 mM, and preferably in the range of 0.8 to 1.2 mM, more preferably about 1.0 mM.
17. The method according to any one of the preceding items, wherein the solution further comprises a buffering compound.
18. The method according to any one of the preceding items, wherein the pH value of the solution is in the range of 5 to 8, preferably in the range of 6 to 7.5.
19. The method according to any one of the preceding items, wherein the solution further comprises a therapeutically relevant concentration of a local anesthetic.
20. The method according to item 19, wherein the local anesthetic is selected from the group consisting of lidocaine and ropivacaine.
21. The method according to any one of the preceding items, wherein the autoclaving is performed at an $F_0$-value>4.
22. The method according to any one of the preceding items, wherein the formed sterilized injectable hydrogel composition exhibits increased stability compared to an identical composition without the divalent cation.
23. A sterilized injectable hydrogel composition obtainable by the method according to any one of items 1-22.
24. A sterilized injectable hydrogel composition comprising
   i) a covalently crosslinked glycosaminoglycan, and
   ii) a divalent cation.
25. The composition according to item 24, wherein the glycosaminoglycan is selected from the group consisting of hyaluronic acid, chondroitin and chondroitin sulfate, and mixtures thereof.
26. The composition according to item 25, wherein the glycosaminoglycan is a hyaluronic acid.
27. The composition according to any one of items 24-26, wherein the crosslinking agent is selected from the group consisting of divinyl sulfone, multiepoxides and diepoxides.
28. The composition according to item 27, wherein the crosslinking agent is selected from the group consisting of 1,4-butanediol diglycidyl ether (BDDE), 1,2-ethanediol diglycidyl ether (EDDE) and diepoxyoctane.
29. The composition according to item 28, wherein the crosslinking agent is 1,4-butanediol diglycidyl ether (BDDE).
30. The composition according to any one of items 24-29, wherein the covalently crosslinked glycosaminoglycan has a degree of modification of 2 mole % or less, such as 1.5 mole % or less, such as 1.25 mole % or less.

31. The composition according to any one of items 24-29, wherein the covalently crosslinked glycosaminoglycan has a degree of modification in the range of 0.1 to 2 mole %, such as in the range of 0.2 to 1.5 mole %, such as in the range of 0.3 to 1.25 mole %.

32. The composition according to any one of items 24-31, wherein the concentration of said glycosaminoglycan is in the range of 1 to 100 mg/ml, such as in the range of 2 to 50 mg/ml, such as in the range of 10 to 30 mg/ml.

33. The composition according to any one of items 24-32, wherein the divalent cation is selected from the group consisting of $Ca^{2+}$, $Cu^{2+}$, $Mg^{2+}$ and $Zn^{2+}$.

34. The composition according to any one of items 24-33, wherein the divalent cation is $Zn^{2+}$.

35. The composition according to any one of items 24-34, wherein the concentration of the divalent cation in the composition is in the range of 0.05 to 4 mM, preferably in the range of 0.05 to 2 mM.

36. The composition according to any one of items 24-35, wherein the divalent cation is $Zn^{2+}$; and wherein the concentration of $Zn^{2+}$ in the solution is in the range of 0.5 to 4 mM, preferably in the range of 0.5 to 2 mM, more preferably in the range of 0.8 to 4 mM, such as 0.8 to 2 mM.

37. The composition according to item 36, wherein the concentration of $Zn^{2+}$ in the solution is in the range of 0.8 to 1.5 mM, and preferably in the range of 0.8 to 1.2 mM, more preferably about 1.0 mM.

38. The composition according to any one of items 24-37, further comprising a buffering compound.

39. The composition according to any one of items 24-38, wherein the pH value of the composition is in the range of 5 to 8, preferably in the range of 6 to 7.5.

40. The composition according to any one of items 24-39, further comprising a therapeutically relevant concentration of a local anesthetic.

41. The composition according to item 40, wherein the local anesthetic is selected from the group consisting of lidocaine and ropivacaine.

42. The composition according to any one of items 24-41, wherein the composition has been subjected to sterilization by autoclaving.

43. The composition according to any one of items 24-42, wherein the composition has been subjected to sterilization by autoclaving at an $F_0$-value>4.

44. The composition according to any one of items 24-43, wherein the composition exhibits increased stability compared to an identical composition without the divalent cation.

45. A sterilized injectable hydrogel composition according to any one of items 23-44 for use as a medicament.

46. A sterilized injectable hydrogel composition according to any one of items 23-44 for use in the treatment of a condition susceptible to treatment with the divalent cation.

47. The sterilized injectable hydrogel composition for use according to item 45 or 46, wherein the composition is injected into the skin of a subject.

48. The sterilized injectable hydrogel composition for use according to item 47, wherein the composition provides a slow release of the divalent cation in the skin of the subject upon injection.

49. The sterilized injectable hydrogel composition for use according to item 47 or 48, wherein the release of the divalent cation in the skin of the subject upon injection is below 0.1 mmol/day.

50. Use of a sterilized injectable hydrogel composition according to any one of items 23-44 for the manufacture of a medicament for treatment of a condition susceptible to treatment with the divalent cation.

51. A method of treating a patient suffering from a condition susceptible to treatment with a divalent cation by administering to the patient a therapeutically effective amount of the sterilized injectable hydrogel composition according to any one of items 23-44.

52. A method of cosmetically treating skin, which comprises administering to the skin a sterilized injectable hydrogel composition according to any one of items 23-44.

BRIEF DESCRIPTION OF THE DRAWINGS

The invention is further illustrated by FIGS. 1-6. FIGS. 1-6 represent exemplary embodiments only.

EXAMPLES

Without desiring to be limited thereto, the present invention will in the following be illustrated by way of examples.

Example 1—Hyaluronic Acid Gel with MoD 1%

A BDDE (1,4-butandiol diglycidylether) crosslinked hyaluronic acid gel with a degree of modification of 1 mole % and a hyaluronic acid content of 20 mg/mL was prepared by first transferring hyaluronic acid (Mw 1 MDa) to a plastic jar. A solution of 1% NaOH and 0.3% BDDE was added and the mixture was homogenized. The jar was transferred to an incubator to perform the crosslinking step. The resulting gel was divided in two parts. The first part was allowed to swell to a HA concentration of about 20 mg/mL in a buffer solution containing sodium phosphate, HCl and NaCl, at a pH about 7.4 (Reference). The second part was allowed to swell to a HA concentration of about 20 mg/mL in a buffer solution containing sodium phosphate, HCl, NaCl and 1 mM $ZnCl_2$. The pH of the formulations was adjusted to 7.4 and the formulations were filled in glass syringes and autoclaved in a Getinge 6610 ERC-1 autoclave ($F_0$~19).

The rheological properties of the formulations were analyzed using an Ahres G2 reometer (measure system PP 40, gap 1.00 mm). Initially a strain sweep was made to find the linear viscoelastic region (LVR) and then the viscoelastic properties were measured within the LVR.

Figure 1A:
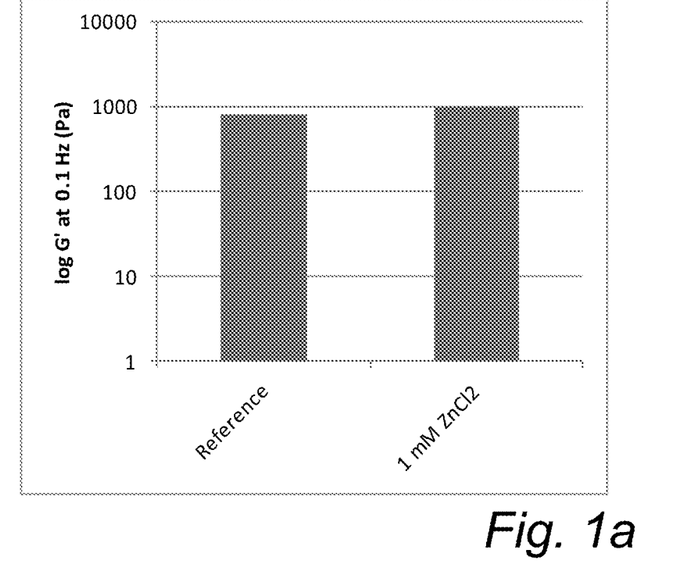
FIG. 1*a* is a diagram showing the stabilizing effect of Zn on a hyaluronic acid gel with a degree of modification of 1 mole %.

FIG. 1*a* shows the difference in G' between the HA gel sample swelled in buffer with $ZnCl_2$ and the Reference sample swelled in buffer only.

A stabilizing effect on the gel can be seen when 1 mM $ZnCl_2$ is used in the formulation.

Example 2—Hyaluronic Acid Gel with MoD 5%

A BDDE (1,4-butandiol diglycidylether) crosslinked hyaluronic acid gel with a of modification of 5 mole % was prepared by mixing 3 g of hyaluronate (Mw 2 MDa) with a mixture of BDDE (1,4-butandiol diglycidylether) in 1% NaOH. The BDDE/NaOH solution was prepared by diluting BDDE in 1% NaOH to get to give a basic BDDE solution diluted to 1/100. 19 g of the prepared BDDE solution was then added to hyaluronate and homogenized. The mixture was placed in a water bath at 50° C. for 2 h.

The resulting crosslinked hyaluronic acid was swelled in phosphate buffer saline (1 mM PBS) and pH was adjusted to 7. The gel was then purified by dialysis (MWCO 15000) for 2 days. The gel was then divided in two parts, to one of the gels 1 M $ZnCl_2$ was added to get a concentration of 1 mM $ZnCl_2$ in the final gel, PBS buffer was added to get a final hyaluronic acid concentration of 20 mg/m L. To the second part of the gel PBS buffer was added to get a final hyaluronic acid concentration of 20 mg/mL. The pH of the formulations was adjusted to 7.4 and the formulations were filled in glass syringes and autoclaved in a Getinge 6610 ERC-1 autoclave ($F_0$~19).

The rheological properties of the formulations were analyzed using an Ahres G2 reometer (measure system PP 40, gap 1.00 mm). Initially a strain sweep was made to find the linear viscoelastic region (LVR) and then the viscoelastic properties were measured within the LVR.

Figure 1B:
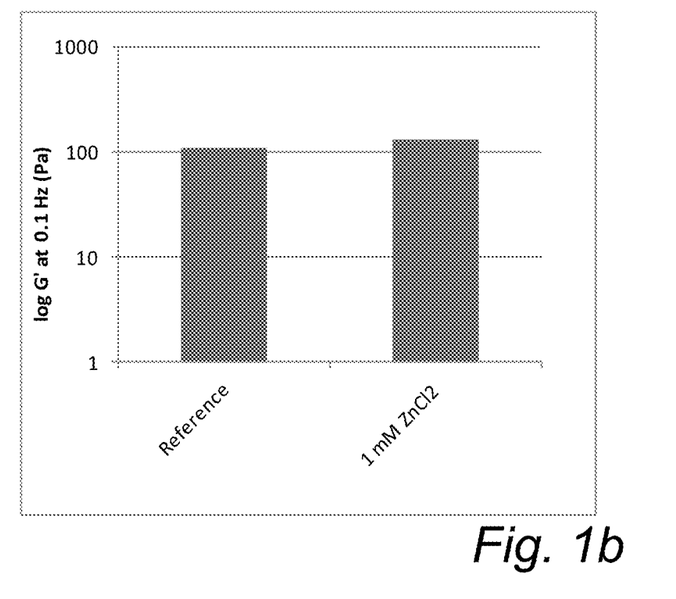
FIG. 1*b* is a diagram showing the stabilizing effect of Zn on a hyaluronic acid gel with a degree of modification of 5 mole %.

FIG. 1b shows the difference in G' between the HA gel sample swelled in buffer with $ZnCl_2$ and the Reference sample swelled in buffer only.

A stabilizing effect on the gel can be seen when 1 mM $ZnCl_2$ is used in the formulation. The stabilizing effect on the gel from the addition of $ZnCl_2$ is thus present both in the case of a gel with 1% and 5% degree of modification.

Example 3—Hyaluronic Acid Gels with Different $ZnCl_2$ Concentrations

A BDDE (1,4-butandiol diglycidylether) crosslinked hyaluronic acid gel with a degree of modification of 1 mole % and a hyaluronic acid content of 20 mg/mL was prepared according to Example 1, with the difference that the gel was divided into 8 parts after the crosslinking step. The gels parts were swelled to about 20 mg/mL with PBS buffer containing 0, 0.01, 0.05, 0.1, 0.5, 1, 2, 4 and 8 mM $ZnCl_2$, respectively. The pH of the formulations was adjusted to 7.4 and the formulations were filled in glass syringes and autoclaved in a Getinge 6610 ERC-1 autoclave ($F_0$~19).

Figure 5A:
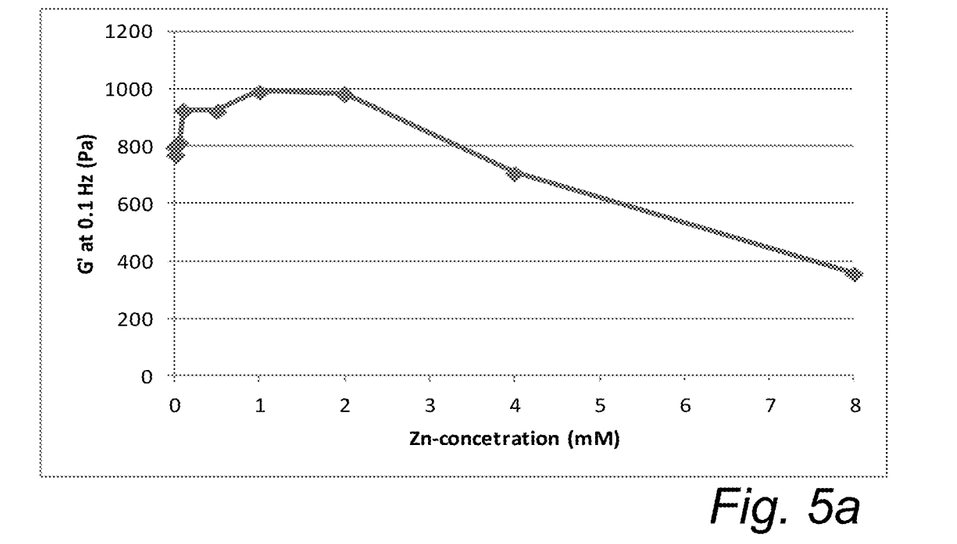
FIG. 5*a* is a diagram showing the concentration dependence of the stabilizing effect of Zn.

FIG. 5a shows the effect on the rheological properties following autoclaving of the gel at different concentrations of $ZnCl_2$.

A stability study was also performed on the gels. Autoclaved syringes were put in an incubator for 1 and 2 weeks and the rheological properties were then analyzed.

Figure 5B:
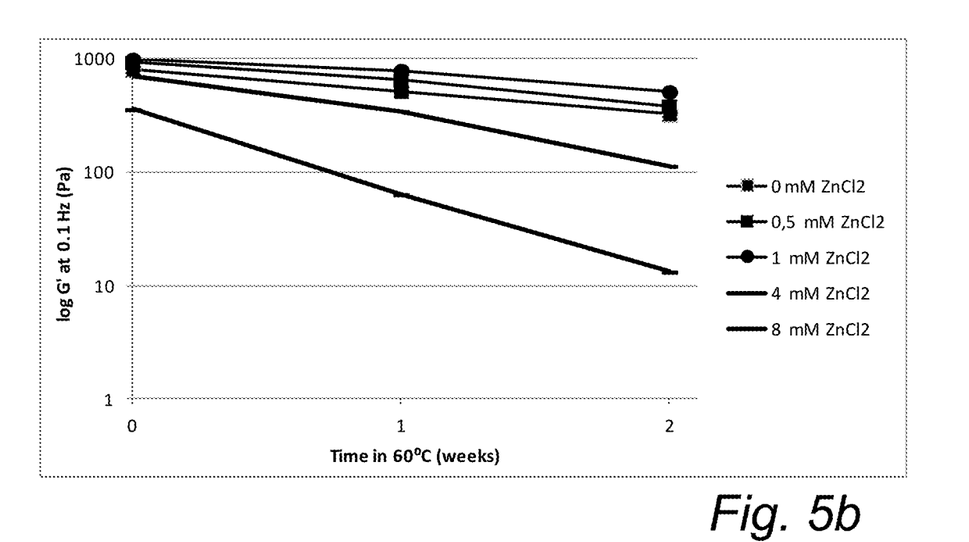
FIG. 5*b* is a diagrams showing the effect of Zn on the storage stability of the composition.

FIG. 5b shows the rheological properties of the gel at different concentrations of $ZnCl_2$ as a function of time when the gels is subjected to 60° C. for 1 and 2 weeks.

A stabilizing effect in the gel was seen with 0.05-2 mM $ZnCl_2$ while degradation of the gel was observed with concentration at 4 mM $ZnCl_2$ and above. The degradation rate of the gel was higher when a higher concentration of $ZnCl_2$ was used.

Example 4—Hyaluronic Acid Gel with Different Zn Salts

A BDDE (1,4-butandiol diglycidylether) crosslinked hyaluronic acid gel with a degree of modification of 1 mole % and a hyaluronic acid content of 20 mg/mL was prepared according to Example 1, with the difference that the gel was divided into 4 parts after the crosslinking step. As shown in Table 1, one part was swelled in PBS buffer (1 mM phosphate), one part was swelled in PBS buffer with 1 mM $ZnCl_2$, one part was swelled in PBS buffer with 1 mM Zn-gluconate and one part was swelled with PBS buffer with 1 mM Zn-citrate. All gels were swelled to a HA concentration of about 20 mg/mL. The pH of the formulations was adjusted to 7.4 and the formulations were filled in glass syringes and autoclaved in a Getinge 6610 ERC-1 autoclave ($F_0$~19).

The rheological properties of the formulations were analyzed using an Ahres G2 reometer (measure system PP 40, gap 1.00 mm). Initially a strain sweep was made to find the linear viscoelastic region (LVR) and then the viscoelastic properties were measured within the LVR.

TABLE 1

| Formulation | HA Gel (mg/mL) | Zn-salt | Zn-salt (mM) | PBS (mM) | G' at 0.1 Hz (kPa) |
|---|---|---|---|---|---|
| 4a | 20 |  | 0 | 1 | 0.80 |
| 4b | 20 | $ZnCl_2$ | 1 | 1 | 0.99 |
| 4c | 20 | Zn-gluconate | 1 | 1 | 1.04 |
| 4d | 20 | Zn-citrate | 1 | 1 | 1.12 |

Figure 4:
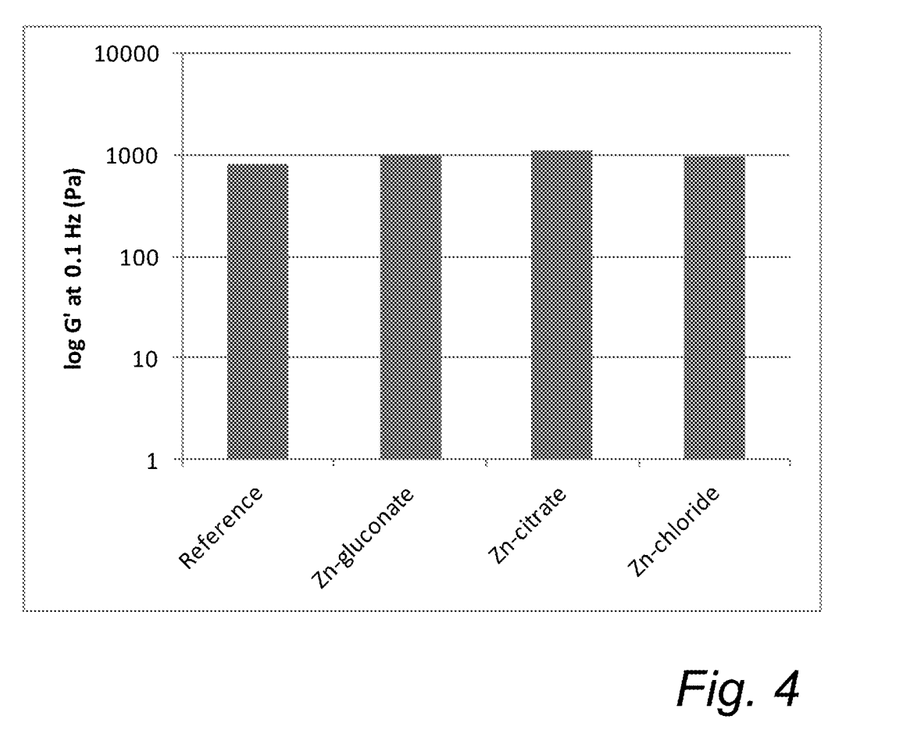
FIG. 4 is a diagram showing that different Zn salts have a similar stabilizing effect.

FIG. 4. shows the difference in G' between an the samples swelled in PBS with 1 mM $ZnCl_2$, 1 mM Zn-gluconate and Zn-citrate and the reference sample swelled in PBS only. A stabilizing effect can be seen when Zn is added either as $ZnCl_2$, Zn-gluconate or Zn-citrate.

Example 5—Hyaluronic Acid Gel with $ZnCl_2$ and Different Buffers

A BDDE (1,4-butandiol diglycidylether) crosslinked hyaluronic acid gel with a degree of modification of 1 mole % and a hyaluronic acid content of 20 mg/mL was prepared and analyzed according to Example 1, with the difference that Tris buffer (50 mM) in saline was used instead of PBS during the swelling of the gel.

Figure 3:
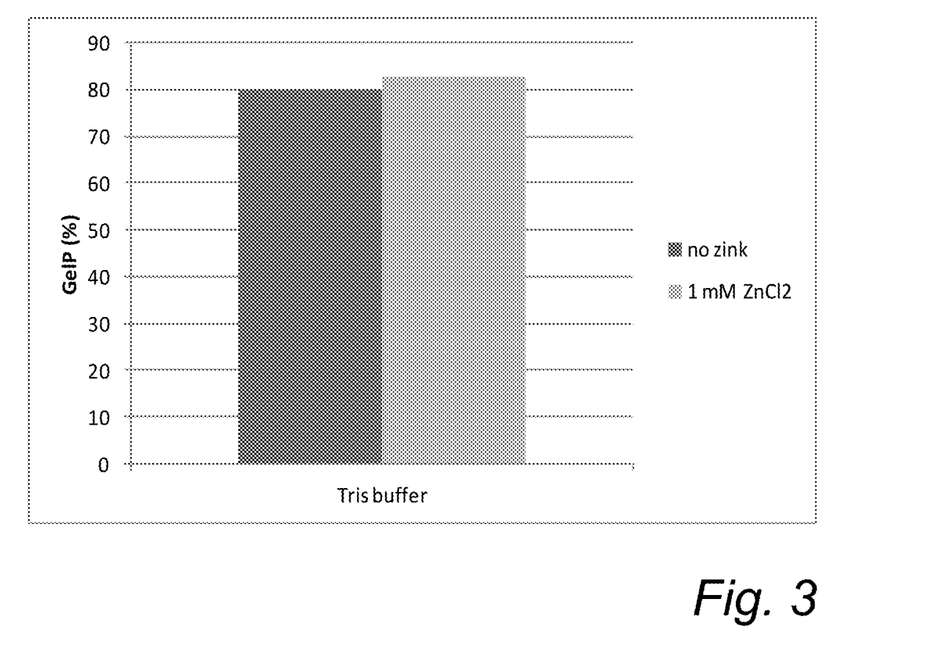
FIG. 3 is a diagram showing that the stabilizing effect of Zn is also present when tris is used as the buffer.

As shown in FIG. 3, the stabilizing effect of 1 mM $ZnCl_2$ after autoclaving is present also when Tris buffer (50 mM) in saline is used in the formulation.

Example 6—HA Gel with Zn and Local Anesthetics

A BDDE (1,4-butandiol diglycidylether) crosslinked hyaluronic acid gel with a degree of modification of 1 mole % and a hyaluronic acid content of 20 mg/mL was prepared according to Example 1, with the difference that the gel was divided into 8 parts after the crosslinking step. The gel parts were swelled in 10 mM PBS buffer with or without 1 mM $ZnCl_2$, according to Table 2.

Stock solutions of lidocaine hydrochloride monohydrate and ropivacaine hydrochloride monohydrate, respectively, were prepared by dissolving lidocaine and ropivacaine in water. The stock solutions were added to the hyaluronic acid gel with 1 mM $ZnCl_2$ and 10 mM phosphate buffer saline to a final concentration of 1 mg/mL for ropivacaine and 3 mg/mL for lidocaine. The gels were homogenized by stirring and pH of the formulations was adjusted to 6.5 or 7.3 according to Table 2 and the formulations were filled in glass syringes and autoclaved in a Getinge 6610 ERC-1 autoclave ($F_0$~19).

The rheological properties of the formulations were analyzed using an Ahres G2 reometer (measure system PP 40, gap 1.00 mm). Initially a strain sweep was made to find the linear viscoelastic region (LVR) and then the viscoelastic properties were measured within the LVR.

TABLE 2

Formulations and rheological data for gels prepared according to Example 6

| Formula-tion | HA Gel (mg/mL) | $ZnCl_2$ (mM) | Lidocaine (mg/mL) | Ropivacaine (mg/mL) | pH | G' at 0.1 Hz (kPa) |
|---|---|---|---|---|---|---|
| 6a | 20 | 0 | 0 | 0 | 7.3 | 0.71 |
| 6b | 20 | 0 | 3 | 0 | 7.3 | 0.74 |
| 6c | 20 | 1 | 0 | 0 | 7.3 | 0.83 |
| 6d | 20 | 1 | 3 | 0 | 7.3 | 0.85 |
| 6e | 20 | 0 | 0 | 0 | 6.6 | 0.80 |
| 6f | 20 | 0 | 0 | 1 | 6.6 | 0.75 |
| 6g | 20 | 1 | 0 | 0 | 6.6 | 0.84 |
| 6h | 20 | 1 | 0 | 1 | 6.5 | 0.86 |

Figure 2A:
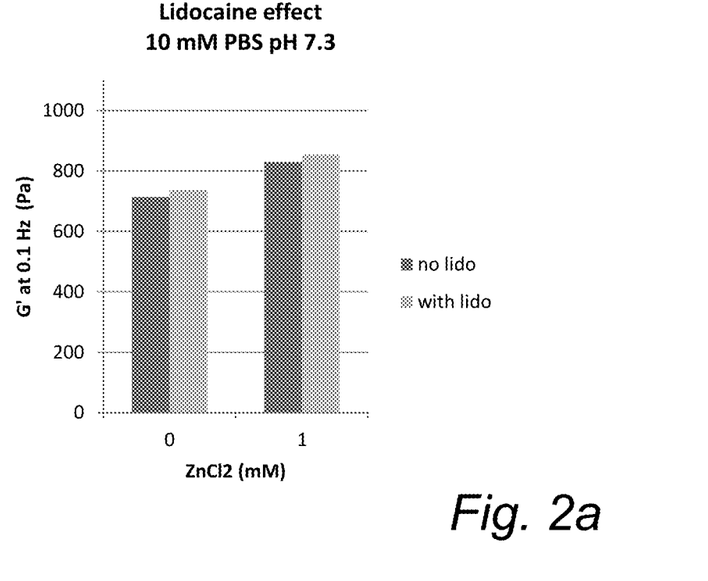
FIGS. 2*a* and 2*b* are diagrams showing that the stabilizing effect of Zn is also present when lidocaine or ropivacaine is added to the composition.
Figure 2B:
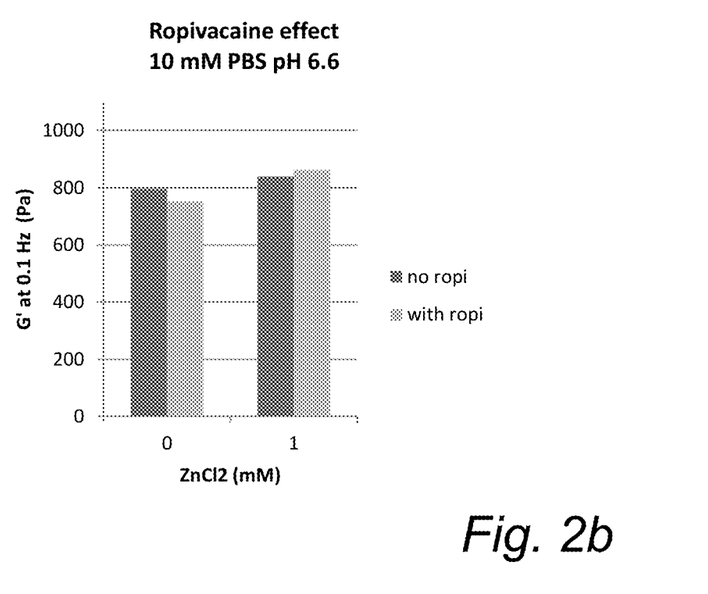

As shown in Table 2 and FIGS. 2a and 2b the stabilizing effect of the 1 mM $ZnCl_2$ on the gel is seen also when a caine is present in the formulation.

Example 7—Release of Zn from a Gel Containing $ZnCl_2$

The zinc release from the gels was measured by the USP-paddle apparatus using special gel containers in which the gel was placed. A gel containing 1 mM $ZnCl_2$ was manufactured according to Example 1. The gel was filled into 7 gel containers with a fixed volume of 1 ml. The geometry of the filled gel was a cylinder 1 cm in diameter and 3 mm deep. The gels were covered by a mesh-size plastic net (PA80 m=200 mesh, AB Derma) and a coarse stainless steel net, care was taken to assure that no air was trapped between the gel and the plastic net.

Each gel container was immersed in 600 ml thermostated release medium, stirred at 30 rpm and maintained at 37° C. using a Distek Evolution 6100 (North Brunswick, N.J.). At predetermined time points, gel containers were removed and the Zn content in the container was determined using ICP.

Figure 6:
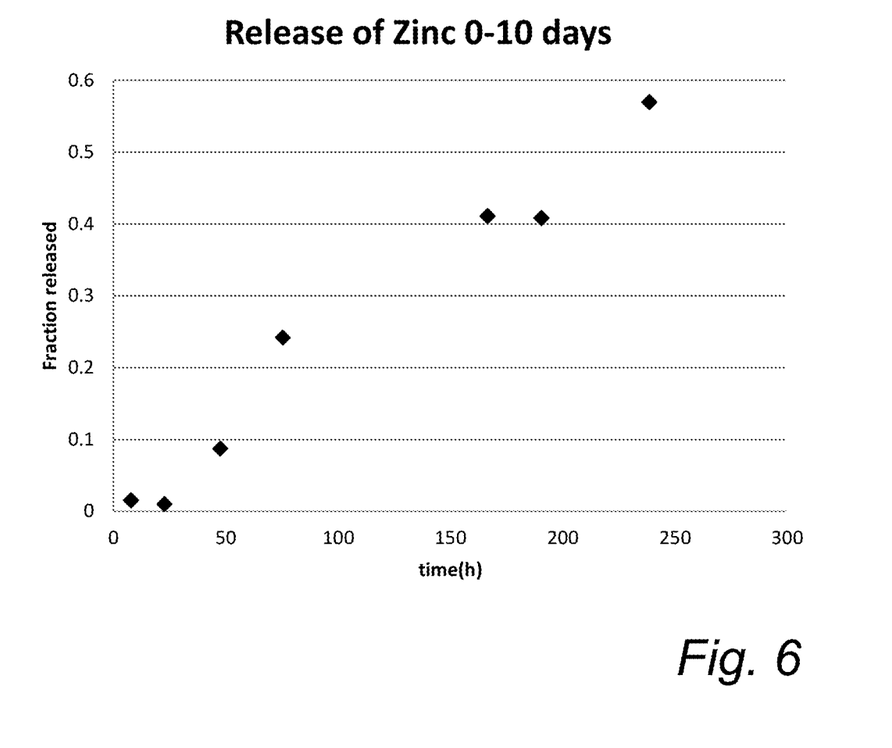
FIG. 6 is a diagram showing the fraction of Zn released from the gel containing 1 mM zinc chloride as a function of time.

The results are shown in FIG. 6. The release of Zn from the gel is very slow. In this experimental setup, a small molecule freely diffusing in a similar gel without any interactions between the gel and the molecule is normally fully released after 6 hours.

After 8 days, less than 50% of the Zn in the gel has been released. This gives a release of ~0.06 µmol/day. These results indicate that the gel could be safely used in vivo to effect a slow release of Zn to a subject.

Example 8—Release of Zn from Gels Containing Different Zinc Salts

Gels prepared according to example 4 containing zinc chloride (1 mM), zinc gluconate (1 mM) and zinc citrate (1 mM) respectively were analyzed as described in Example 7. Table 3 shows the relative release rate for the different zinc salts.

TABLE 3

Time for 25% release zinc for the different salts

| Salt | time for 25% released | % dissociation of salt (free $Zn^{2+}$, reference M) |
|---|---|---|
| zinc chloride | ~75 hours | 100 |
| zinc gluconate | ~24 hours | 30 |
| zinc citrate | ~3 hours | 0 |

A larger fraction of dissociated zinc (free $Zn^{2+}$) results in a slower release, probably as a result of the interaction between Zn and the hyaluronan in the gel. The zinc that is complexed with its counterion will not interact with the gel, and the larger the fraction of zinc that is complexed with its counterion, the more rapid is the release.

The invention claimed is:

1. A sterilized injectable hydrogel composition, comprising:
    (i) a covalently crosslinked glycosaminoglycan, wherein the glycosaminoglycan is hyaluronic acid, and
    (ii) a divalent cation, wherein the divalent cation is $Zn^{2+}$, and wherein the concentration of $Zn^{2+}$ in the composition is in the range of 0.5 to 2 mM;
    wherein the composition releases the divalent cation at a rate below 0.1 mmol/day upon injection into a subject, and
    wherein the composition has been subjected to sterilization by autoclaving.

2. The composition according to claim 1, wherein the concentration of the divalent cation in the composition is in the range of 0.8 to 2 mM.

3. The composition according to claim 2, wherein the concentration of $Zn^{2+}$ in the composition is in the range of 0.8 to 1.5 mM.

4. The composition according to claim 3, wherein the concentration of $Zn^{2+}$ in the composition is about 1.0 mM.

5. The composition according to claim 1, further comprising a therapeutically relevant concentration of a local anesthetic selected from the group consisting of lidocaine and ropivacaine.

6. The composition according to claim 1, wherein the composition exhibits increased stability compared to an identical composition without the divalent cation.

7. A method of preparing a sterilized injectable hydrogel composition comprising:
    (i) a covalently crosslinked glycosaminoglycan, wherein the glycosaminoglycan is hyaluronic acid, and
    (ii) a divalent cation, wherein the divalent cation is $Zn^{2+}$, and the concentration of $Zn^{2+}$ in the composition is in the range of 0.5 to 2 mM;
    wherein the composition releases the divalent cation at a rate below 0.1 mmol/day upon injection into a subject, the method comprising:
    (a) covalently crosslinking a glycosaminoglycan using a bi- or polyfunctional crosslinking agent to form a covalently crosslinked glycosaminoglycan, wherein the glycosaminoglycan is hyaluronic acid, and
    (b) swelling the covalently crosslinked glycosaminoglycan in a solution comprising Zn2+, to form a hydrogel composition, wherein the concentration of Zn2+ in the solution is in the range of 0.5 to 2 mM; and
    (c) sterilizing the hydrogel composition by autoclaving to form the sterilized injectable hydrogel composition.

8. The method according to claim 7, wherein the concentration of $Zn^{2+}$ in the solution is in the range of 0.8 to 2 mM.

9. The method according to claim 8, wherein the concentration of $Zn^{2+}$ in the solution is in the range of 0.8 to 1.5 mM.

10. The method according to claim 8, wherein the concentration of $Zn^{2+}$ in the solution is about 1.0 mM.

11. The method according to claim 7, wherein the solution further comprises a therapeutically relevant concentration of a local anesthetic selected from the group consisting of lidocaine and ropivacaine.

12. The method according to claim 7, wherein the sterilized injectable hydrogel composition exhibits increased stability compared to an identical composition without the divalent cation.

13. A method of cosmetically treating skin, the method comprising administering to the skin the sterilized injectable hydrogel composition according to claim 1.

14. The composition according to claim 1, wherein the glycosaminoglycan is in the range of 5 to 30 mg/mL.

15. The composition according to claim 1, wherein the divalent cation is added as a zinc salt.

16. The composition according to claim 15, wherein the zinc salt is selected from zinc chloride, zinc gluconate, or zinc citrate.

* * * * *